United States Patent
Atzinger

(10) Patent No.: US 9,820,707 B2
(45) Date of Patent: Nov. 21, 2017

(54) X-RAY DEVICE

(71) Applicant: Michael Atzinger, Seybothenreuth (DE)

(72) Inventor: Michael Atzinger, Seybothenreuth (DE)

(73) Assignee: Siemens Aktiengesellschaft, München (DE)

( * ) Notice: Subject to any disclaimer, the term of this patent is extended or adjusted under 35 U.S.C. 154(b) by 176 days.

(21) Appl. No.: 14/614,922

(22) Filed: Feb. 5, 2015

(65) Prior Publication Data
US 2015/0216494 A1 Aug. 6, 2015

(30) Foreign Application Priority Data

Feb. 5, 2014 (DE) .................. 10 2014 202 013

(51) Int. Cl.
*A61B 6/00* (2006.01)
*H01L 27/146* (2006.01)
(Continued)

(52) U.S. Cl.
CPC .......... *A61B 6/4441* (2013.01); *A61B 6/4429* (2013.01); *A61B 6/4435* (2013.01);
(Continued)

(58) Field of Classification Search
CPC .... A61B 6/00; A61B 6/42; A61B 6/44; A61B 6/4429; A61B 6/4435; A61B 6/4411; A61B 2560/00; A61B 2560/04; A61B 2560/0406; A61B 2562/00; A61B 2562/22; A61B 2562/225; H01L 27/14; H01L 27/144; H01L 27/146; H01L 27/14601; H01L 27/14618; H01L 27/14636; H01L 27/14658; H01L 27/14676; H01L 27/148;
(Continued)

(56) References Cited

U.S. PATENT DOCUMENTS 5,773,909 A * 6/1998 Hansen ................. H01J 35/101
310/166
6,590,953 B2 * 7/2003 Suzuki .................. A61B 6/035
310/211

(Continued)

FOREIGN PATENT DOCUMENTS

CN 101398398 A 4/2009
CN 10321612 A 7/2013
(Continued)

OTHER PUBLICATIONS

ETEL Innovative Motion Control, "Direct Drive Tprque Motor Principle", retrieved Mar. 29, 2017 from http://www.etel.ch/torque-motors/principle/, pp. 1-2.*

(Continued)

*Primary Examiner* — Anastasia Midkiff
(74) *Attorney, Agent, or Firm* — Lempia Summerfield Katz LLC

(57) ABSTRACT

An X-ray device includes a C-bracket having a radiation detector rotatably mounted on the C-bracket. The radiation detector may be rotated by a motor drive. The axis of rotation is perpendicular to the detector surface. The motor drive is a torque motor that includes a stator and a rotor. The radiation detector is coupled to the rotor.

17 Claims, 3 Drawing Sheets

(51) Int. Cl.
*H01L 27/148* (2006.01)
*H05G 1/02* (2006.01)
*A61B 6/03* (2006.01)

(52) U.S. Cl.
CPC .. *H01L 27/14601* (2013.01); *H01L 27/14806* (2013.01); *H05G 1/02* (2013.01); *A61B 6/035* (2013.01); *A61B 2560/04* (2013.01); *A61B 2562/22* (2013.01); *A61B 2562/225* (2013.01); *G01N 2223/30* (2013.01); *G01N 2223/321* (2013.01)

(58) Field of Classification Search
CPC ... H01L 27/14806; H01L 25/00; H01L 25/03; G01N 2223/00; G01N 2223/30; G01N 2223/321; G01N 2223/3303; G01N 2223/50; H05G 1/00; H05G 1/02
See application file for complete search history.

(56) References Cited

U.S. PATENT DOCUMENTS

| | | | |
|---|---|---|---|
| 8,170,175 B2* | 5/2012 | Kasuya | A61B 6/035 378/15 |
| 2002/0118793 A1* | 8/2002 | Horbaschek | A61B 6/4233 378/197 |
| 2006/0198497 A1 | 9/2006 | Gotoh | |
| 2007/0140437 A1* | 6/2007 | Gotoh | A61B 6/4441 378/197 |
| 2009/0080599 A1* | 3/2009 | Kasuya | A61B 6/035 378/15 |
| 2012/0275563 A1* | 11/2012 | Manak | A61B 6/00 378/62 |
| 2014/0233702 A1* | 8/2014 | Suzuki | A61B 6/42 378/62 |

FOREIGN PATENT DOCUMENTS

| | | |
|---|---|---|
| CN | 101116619 A | 4/2014 |
| CN | 103732144 A | 4/2014 |
| EP | 2086413 B1 | 7/2013 |
| JP | 2006055328 A | 3/2006 |
| WO | WO2008055517 A1 | 5/2008 |

OTHER PUBLICATIONS

Wikipedia, "Torque Motor", retrieved Mar. 29, 2017 from https://en.wikipedia.org/wiki/Torque_motor, pp. 1-2.*
TorqueTec, "Direct Drive Technology", retrieved Mar. 29, 2017 from http://www.torquetec.de, pp. 1-16.*
German Office Action for German Application No. 10 2014 202 013.1, dated Oct. 22, 2014, with English Translation.
Chinese Office Action for related Chinese Patent Application No. 201510060938.7, dated Feb. 4, 2017, with English translation.
Chinese Office Action for related Chinese Application No. 201510060938.7 dated Sep. 18, 2017.

* cited by examiner

X-RAY DEVICE

RELATED APPLICATIONS

This application claims the benefit of German Patent Application No. DE 102014202013.1, filed Feb. 5, 2014. The entire contents of the priority document are hereby incorporated herein by reference.

TECHNICAL FIELD

The present teachings relate generally to x-ray devices. In some embodiments, an x-ray device includes a C-bracket having a radiation detector rotatably mounted thereon. The radiation detector may be rotated by a motor drive, and the axis of rotation is perpendicular to the detector surface.

BACKGROUND

In medical imaging technology, x-ray devices may be used for recording radiation images. An x-ray device may have a C-bracket that may be moved about several axes. The C-bracket may be positioned relative to the object under investigation (e.g., a patient) depending on the research task. A radiation source (e.g., an x-ray radiation source) is arranged on one end of the C-bracket, and a radiation detector (e.g., a "flat detector") having a radiation-sensitive image-recording matrix is arranged on the opposite end of the bracket. The x-ray radiation is shaped in an appropriate manner by a corresponding masking device associated with the radiation source. The corresponding radiation image is recorded or read out at the radiation detector and subjected to image processing by a control device.

When x-ray devices are used in angiography, the radiation detector may be turned about a central axis (e.g., about an axis of rotation that is perpendicular to the image recording or detector surface). The rotation facilitates production of portrait- or landscape-format images with what may be a rectangular detector surface. To keep the alignment of the image detector constant relative to the patient while the C-bracket is moving relative to the patient during image recording, a motor drive for rotating the radiation detector may be provided. A geared motor may be used as a motor drive. The drive includes an electric motor with an associated gear. The radiation detector is mounted in a rotary bearing assembly on the detector and is coupled mechanically to the gear. Although rotation of the detector may be effected with this kind of a drive, there may be problems in achieving the required positioning accuracy (e.g., detector rotation during a movement of the C-bracket). As a result, image quality may be poorer as compared to images recorded with a stationary radiation detector.

SUMMARY AND DESCRIPTION

The scope of the present invention is defined solely by the appended claims, and is not affected to any degree by the statements within this summary.

The present embodiments may obviate one or more of the drawbacks or limitations in the related art. For example, in some embodiments, an x-ray device is provided that allows rotation of the detector with high positioning accuracy.

In accordance with the present teachings, a motor drive for an x-ray device may be a torque motor that includes a stator and a rotor, wherein the radiation detector is coupled to the rotor.

In accordance with the present teachings, a torque motor may be used as a drive motor instead of a conventional electric motor-gear unit. The torque motor includes a stator and a rotor. The stator is fixed in position relative to the C-bracket, and the rotor rotates relative to the stator with extremely high positioning accuracy. In accordance with the present teachings, the radiation detector is coupled to the rotor. A torque motor as a direct drive is distinguished by the absence of mechanical transmission elements (e.g., gearwheels or a gear). The output shaft (e.g., the rotor) is simultaneously the motor shaft, thereby resulting in very high torsional stiffness and freedom from backlash in the drive train. Freedom from backlash in the drive train is a precondition for highly precise movement and, therefore, high positioning accuracy. A torque motor may be used to achieve a positioning accuracy of 0.02 angular degrees or less with an x-ray device in accordance with the present teachings.

Due to the relatively large diameters of the rotor, a correspondingly high torque is produced. The high torque may be advantageous for positional accuracy and accurate, reproducible rotation of the detector.

The axis of rotation of the rotor is perpendicular to the detector or image-recording surface. The radiation detector is coupled to the rotor with respect to motion, such that the axis of rotation passes through the center of the detector surface and, therefore, the central pixel.

The radiation detector may be connected directly to the rotor. For example, complementary connection parts may be provided on the rotor side and the detector side for connecting the radiation detector and the rotor. Alternatively, an adapter may be arranged between the rotor and the radiation detector and connecting the two together. The adapter may be arranged on each of the rotor and the radiation detector by appropriate connection parts.

Regardless of whether the radiation detector is arranged directly on the rotor, or the rotor and the radiation detector are coupled by an adapter, screw connections may be used for connection parts, thereby facilitating disassembly of the individual interconnected components for maintenance purposes.

For screw fastening, the detector may have a mounting plate having a plurality of apertures configured for receiving the screws. The rotor also has a plurality of holes into which the screws may be screwed. If an adapter is used, the adapter has a corresponding pattern of holes configured for receiving the screws that connect the rotor to the adapter and the screws that screw the radiation detector to the adapter. The adapter may be used to connect radiation detectors of different sizes (e.g., detectors with image recording surfaces of different sizes) to the same torque motor.

If a detector-side mounting plate is used, the mounting plate may be arranged on the outside of a housing of the radiation detector. For example, the mounting plate may be screwed to the housing or may form part of the housing. Alternatively, the mounting plate may be arranged in the interior of the housing. For example, the housing may have an opening facing the rotor or the adapter. A leading edge of the rotor or the adapter engages in the housing through the opening so as to be screwed to the mounting plate. In some embodiments, if the mounting plate is situated in the housing, a detector unit having the actual matrix subject to the action of radiation may be arranged on the side of the mounting plate facing away from the rotor or adapter by holding elements. In some embodiments, the detector unit may be arranged on the mounting plate with a spacing therebetween. The dimensioning of the mounting plate may correspond substantially to the dimensioning of the detector unit. The detector unit (e.g., the constructional unit having the pixel matrix subject to the action of radiation) is firmly connected to the mounting plate. The mounting plate in turn is firmly connected to the rotor or the adapter. A mechanically firm coupling of the matrix subject to the action of radiation to the actual rotary element (e.g., the rotor) is thus provided. As a result, there is no backlash or any tolerances within the chain that could lead to positioning inaccuracies.

To maximize the compactness of the constructional unit, a hollow-cylindrical, housing-type projection that the cylindrical torque motor is inserted into may be provided on the C-bracket. The torque motor may be within the bracket or accommodated within the cylindrical, housing-type projection. For example, the torque motor may be inserted to such an extent that the rotor may still be connected to the radiation detector, mounting plate, or adapter. The housing of the radiation detector may also have a hollow-cylindrical projection that fits at least partially around the outside of the projection of the C-bracket, thereby providing a closed unit.

DETAILED DESCRIPTION

Figure 1:
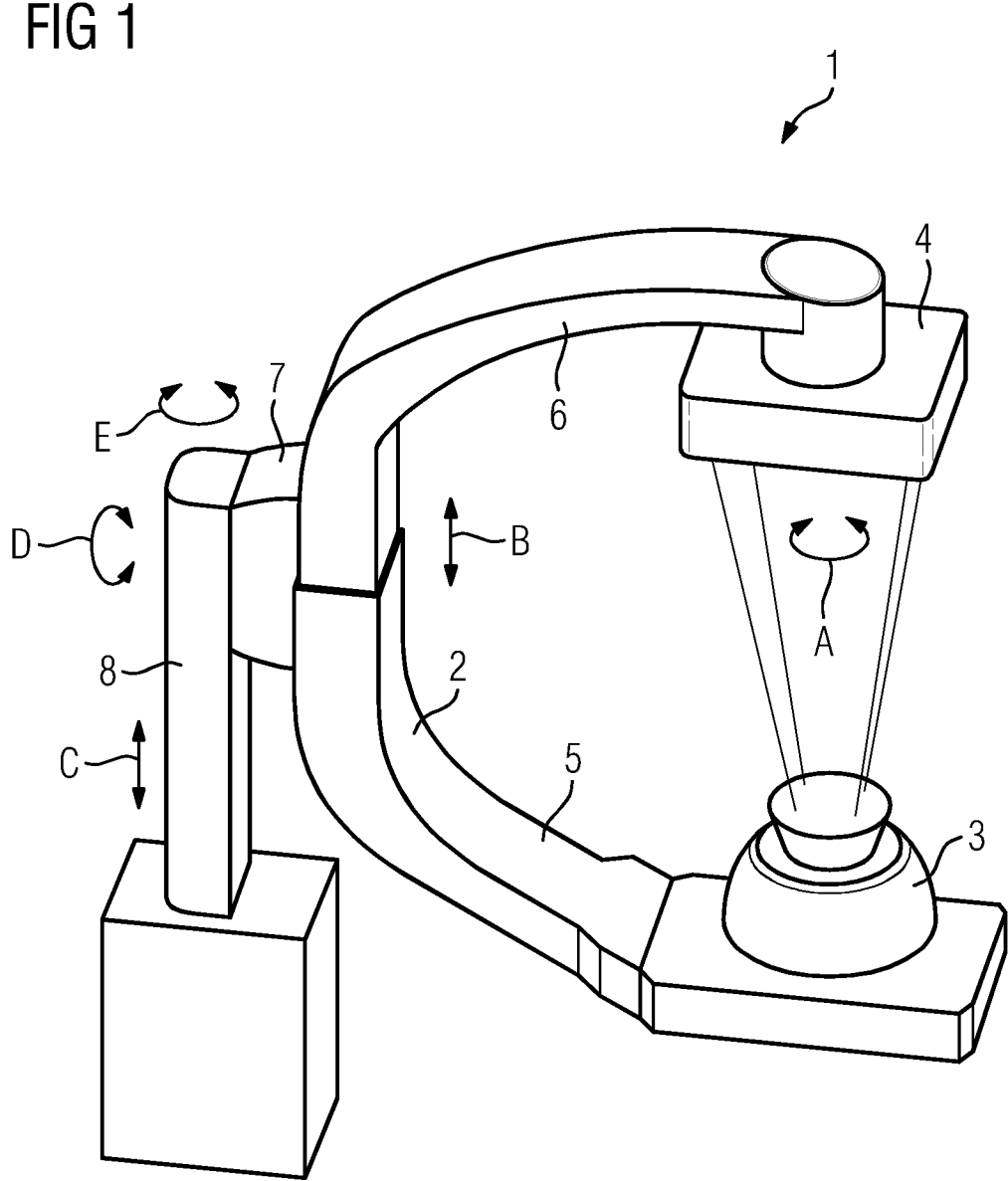
FIG. 1 shows a perspective view of an example of an x-ray device in accordance with the present teachings.

FIG. 1 shows an x-ray device 1 in accordance with the present teachings. The x-ray device 1 includes a C-bracket 2. A radiation source 3 (e.g., an x-ray radiation source) is arranged on one end of the C-bracket 2, and a radiation detector 4 (e.g., a flat-image detector including a radiation-sensitive pixel matrix) is arranged on the other end of the C-bracket 2. As further described below, the radiation detector 4 may be rotated about an axis of rotation perpendicular to the image-recording or matrix plane by a drive part (e.g., in the form of a torque motor), as indicated by the double arrow A.

In the illustrative embodiment shown in FIG. 1, the C-bracket 2 has a first bracket section 5 and a second bracket section 6. As indicated by the double arrow B, the first bracket section 5 and the second bracket section 6 may be moved relative to one another to vary the distance between the radiation source 3 and the radiation detector 4.

The C-bracket 2 is situated on a support unit 7. The support unit 7 is arranged on a column 8. The support unit 7 may be moved vertically along the column 8, as indicated by the double arrow C. The support unit 7 may also be turned relative to the column 8 about a horizontal axis, as indicated by the double arrow D. Thus, the entire C-bracket 2 may be moved vertically and also turned about a horizontal axis.

In addition, the column 8 may be turned about a vertical axis, as indicated by the double arrow E. The basic construction of a C-bracket, the mounting of a C-bracket, and the individual degrees of freedom of a C-bracket will be understood by one of ordinary skill.

Figure 2:
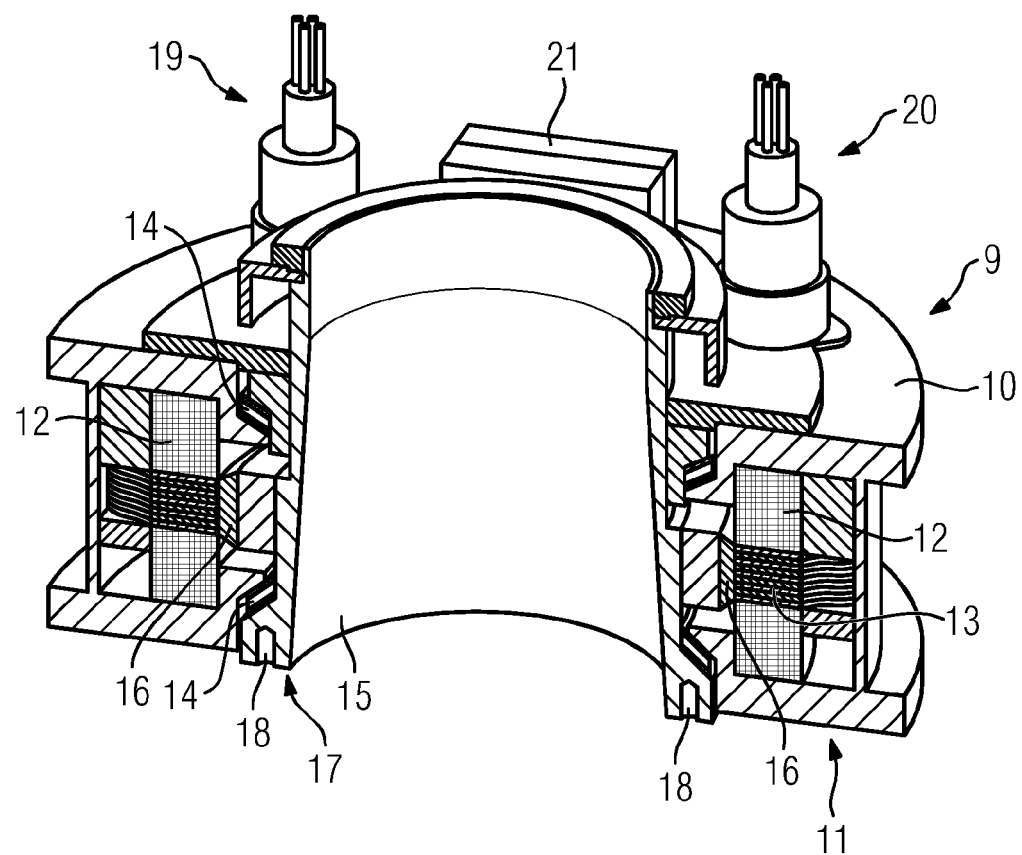
FIG. 2 shows a partial cross-sectional view of an example of a torque motor integrated into a C-bracket of an x-ray device in accordance with the present teachings.

The radiation detector 4 may be turned about an axis perpendicular to the image-recording plane thereof. For this purpose, a motor drive may be used. In accordance with the present teachings, the motor drive may be a torque motor (e.g., a direct drive). FIG. 2 shows a cross-sectional illustration of a torque motor 9. The torque motor 9 has a motor housing 10 that accommodates a stator 11 containing encapsulated winding heads 12 and stator laminations 13. The housing 10 is arranged in a fixed position on the C-bracket 2. The stator 11, therefore, is likewise arranged in a fixed position on the C-bracket 2.

A rotor 15 is mounted in the housing 10 so as to be rotatable relative to the stator 11 by bearings 14. Magnets 16 that interact with the magnetic field produced at the stator are arranged on the outside of the rotor. The rotation of the rotor may be brought about in a conventional manner. A plurality of threaded holes 18 configured to receive fastening screws for connecting the radiation detector 4 to the rotor, as further described below is provided. The threaded holes 18 may be provided at equidistant intervals on the lower end face 17 of the rotor 15.

As shown in FIG. 2, first line connection 19 and second line connection 20 may be used to operate the torque motor 9 (e.g., to energize the winding heads of the stator) or to connect to the image detector for acquiring the measurement signals from the pixels.

An inductively operating measurement system 21 that is used to determine the relative position of the rotor 15 may be provided to accurately detect and monitor the position of the coupled solid-body detector.

Figure 3:
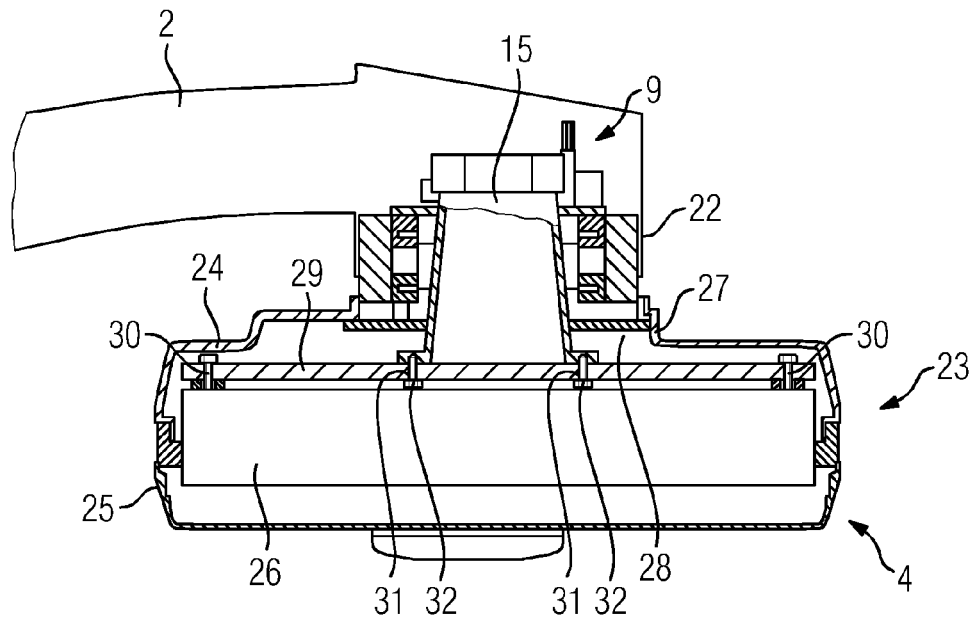
FIG. 3 shows a cross-sectional view of an example of a C-bracket with an integrated torque motor and a radiation detector arranged thereon.

FIG. 3 shows an enlarged cross-sectional detail of the C-bracket 2 with an integrated torque motor 9 and a solid-body radiation detector 4 arranged thereon. The C-bracket 2 has, at an end thereof, a hollow-cylindrical, housing-type projection 22. The cylindrical torque motor 9 is inserted into the hollow-cylindrical, housing-type projection 22. The motor housing 10 is connected to the C-bracket (e.g., via screw). Thus, threaded holes or the like may be provided on the motor housing 10.

The solid-body radiation detector 4 has a housing 23 that includes an upper housing part 24 and a lower housing part 25. The actual detector unit 26 that has the radiation-sensitive pixel matrix is accommodated in the housing 23. The housing 23 or the upper housing part 24 has a projection 27 that may likewise be hollow-cylindrical, for example. The hollow-cylindrical projection 27 fits around the hollow-cylindrical, housing-type projection 22 of the C-bracket 2 with a small clearance in the assembled position. As shown in FIG. 3, a closed unit is thus provided. The hollow-cylindrical projection 27 defines a corresponding opening 28. The leading end face 17 of the rotor 15 projects into the opening 28 as far as a mounting plate 29. The mounting plate 29 is firmly connected to the detector unit 26 by screw connections 30 or similar mechanically fixed couplings. The mounting plate 29 has apertures 31 that are arranged to match the hole pattern of the threaded holes 18 in the rotor 15. Screws 32 screwed into the threaded holes 18 in the rotor 15 engage through the apertures 31. Thus, the radiation detector 4 is connected directly to the rotor 15. A mechanically fixed connection that is substantially free from play or tolerances is provided between the drive element (e.g., the rotor 15) and the detector unit 24. As a result, rotor rotation 15 leads to direct rotation of the radiation detector 4.

Figure 4:
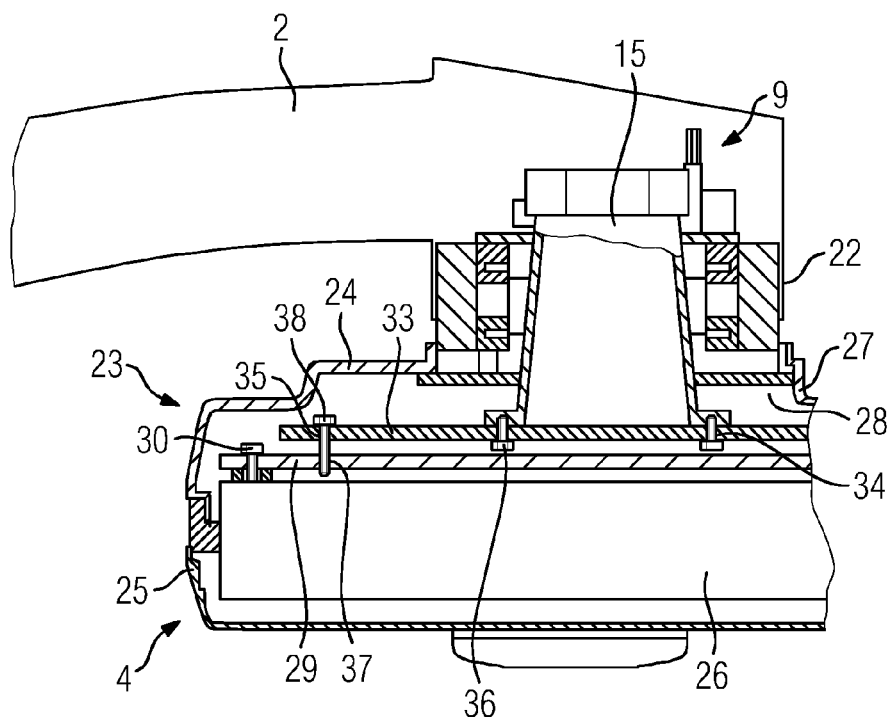
FIG. 4 shows a cross-sectional view of an example of a rotor connected with a radiation detector by an adapter.

FIG. 4 shows an embodiment wherein the rotor 15 is not connected directly to the radiation detector 4 or the mounting plate 29 but rather is connected via an adapter 33. The adapter 33 (e.g., a disk or the like) has first apertures 34. The arrangement of the first apertures 34 corresponds to the hole pattern of the threaded holes 18 in the rotor 15. The adapter 33 is connected firmly to the rotor 15 by screws 36 screwed into the adapter. Additional holes 35 that likewise correspond to the hole pattern of threaded holes 37 in the mounting plate 29 are provided in the adapter 33 in a position that is further radially removed. The mounting plate 29 is screwed firmly to the adapter 33 by screws 38.

The housing-type projection 22 in the embodiment shown in FIG. 4 is analogous to the housing-type projection 22 described above. However, the configuration of the housing 23 or upper housing part 24 of the radiation detector 4 is somewhat different. In FIG. 4, the opening that the adapter 33 engages through in the housing 23 is substantially larger.

Since, as shown in FIG. 4, the detector unit 26 is firmly connected to the mounting plate 29, the mounting plate in turn is firmly connected to the adapter 33, and the latter 33 is connected to the rotor 15, a mechanically play- and tolerance-free connection between the torque motor and the radiation detector is provided. As a result, rotor rotation leads to direct detector rotation.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim-whether independent or dependent-and that such new combinations are to be understood as forming a part of the present specification.

The invention claimed is:

1. An x-ray device comprising:
   a C-bracket; and
   a radiation detector rotatably mounted on the C-bracket,
   wherein the radiation detector is configured to be rotated by a torque motor, the torque motor comprising a stator and a rotor,
   wherein the radiation detector is detachably connected to the rotor, and
   wherein an axis of rotation of the radiation detector is perpendicular to a surface of the radiation detector.

2. The x-ray device of claim 1, wherein the radiation detector is connected directly to the rotor.

3. The x-ray device of claim 1, wherein the radiation detector comprises a mounting plate, the mounting plate comprising a plurality of apertures, each aperture of the plurality of apertures being configured for receiving a screw; and
   wherein the rotor comprises a plurality of threaded holes, each threaded hole of the plurality of threaded holes being configured to receive the screw.

4. The x-ray device of claim 3, wherein the mounting plate is arranged on an outside or an interior of a housing of the radiation detector, the housing comprising an opening that faces towards the rotor.

5. The x-ray device of claim 1, further comprising a detector unit,
   wherein the radiation detector comprises a mounting plate, and
   wherein the detector unit is arranged by holding elements on the mounting plate on a side of the mounting plate facing away from the rotor.

6. The x-ray device of claim 5, wherein dimensioning of the mounting plate corresponds substantially to dimensioning of the detector unit.

7. The x-ray device of claim 1, wherein the C-bracket comprises a hollow-cylindrical, housing-type projection configured for receiving a cylindrical torque motor.

8. The x-ray device of claim 7, wherein a housing of the radiation detector comprises a hollow-cylindrical projection configured to fit around an outside of the hollow-cylindrical housing-type projection of the C-bracket.

9. The x-ray device of claim 1, wherein an adapter is arranged between the rotor and the radiation detector.

10. The x-ray device of claim 1, wherein the rotor and the radiation detector are detachably connected by a screw connection to an adapter, the adapter being arranged between the rotor and the radiation detector.

11. The x-ray device of claim 10, wherein the radiation detector comprises a mounting plate, the mounting plate comprising a plurality of apertures, each aperture of the plurality of apertures being configured for receiving a screw; and
    wherein the adapter comprises a plurality of threaded holes, each threaded hole of the plurality of threaded holes being configured to receive the screw.

12. The x-ray device of claim 11, wherein the mounting plate is arranged on an outside or an interior of a housing of the radiation detector, the housing comprising an opening that faces towards the adapter.

13. The x-ray device of claim 10, further comprising a detector unit,
    wherein the radiation detector comprises a mounting plate, and
    wherein the detector unit is arranged by holding elements on the mounting plate on a side of the mounting plate facing away from the adapter.

14. The x-ray device of claim 13, wherein dimensioning of the mounting plate corresponds substantially to dimensioning of the detector unit.

15. An x-ray device comprising:
    a C-bracket; and
    a radiation detector rotatably mounted on the C-bracket,
    wherein the radiation detector is configured to be rotated by a torque motor, the torque motor comprising a stator and a rotor,
    wherein the radiation detector is connected directly to the rotor, and
    wherein an axis of rotation of the radiation detector is perpendicular to a surface of the radiation detector.

16. An x-ray device comprising:
    a C-bracket;
    a radiation detector rotatably mounted on the C-bracket; and
    an adapter,
    wherein the radiation detector is configured to be rotated by a torque motor, the torque motor comprising a stator and a rotor,
    wherein the radiation detector is coupled to the rotor,
    wherein the adapter is arranged between the rotor and the radiation detector, and
    wherein an axis of rotation of the radiation detector is perpendicular to a surface of the radiation detector.

17. An x-ray device comprising:
a C-bracket;
a radiation detector rotatably mounted on the C-bracket; and
an adapter,
wherein the radiation detector is configured to be rotated by a torque motor, the torque motor comprising a stator and a rotor,
wherein the radiation detector is detachably connected to the rotor by a screw connection to the adapter, the adapter being arranged between the rotor and the radiation detector, and
wherein an axis of rotation of the radiation detector is perpendicular to a surface of the radiation detector.

* * * * *